United States Patent [19]

Tomalia

[11] 4,257,970
[45] Mar. 24, 1981

[54] NOVEL SULFONYL IMIDE INTERMEDIATES

[75] Inventor: Donald A. Tomalia, Midland, Mich.

[73] Assignee: The Dow Chemical Company, Midland, Mich.

[21] Appl. No.: 76,112

[22] Filed: Sep. 17, 1979

[51] Int. Cl.³ .................. C07C 143/74; C07C 143/90
[52] U.S. Cl. .................. 260/401; 260/402; 564/91; 564/98
[58] Field of Search .............. 260/556 AC, 401, 402

[56] References Cited

U.S. PATENT DOCUMENTS 1,916,604  7/1933  Carswell et al. ............. 260/556 AC
4,120,804  10/1978  Smith et al. .................... 252/47.5

OTHER PUBLICATIONS

R. H. Wiley et al., Chemical Reviews, vol. 44, pp. 468–469 (1949).
W. Seeliger et al., Angew. Chem. Internat. Ed., vol. 5, p. 879 (1966).

Primary Examiner—Jacqueline V. Howard
Attorney, Agent, or Firm—Michael L. Glenn

[57] ABSTRACT

Novel N-(haloalkyl)sulfonyl imides represented by the formula

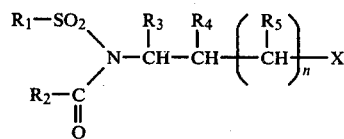

are prepared by the reaction of a 2-alkyl- or 2-aryl-oxazoline or oxazine with an arylene or alkane sulfonyl halide. In the formula for the novel sulfonyl imide, $R_1$ and $R_2$ are each independently $C_1$–$C_{20}$ aryl, alkaryl or alkyl groups; $R_3$, $R_4$ and $R_5$ are each hydrogen or methyl groups; n is the integer 0 or 1 and X is a chloro, bromo or iodo group. These novel sulfonyl imides are particularly useful in the preparation of N-(2-chloroethyl)- and N-(3-chloropropyl)sulfonamides.

8 Claims, No Drawings

NOVEL SULFONYL IMIDE INTERMEDIATES

BACKGROUND OF THE INVENTION

This invention relates to novel N-(haloalkyl)-sulfonyl imides which are useful as chemical intermediates and a process for preparing these compounds.

N-(2-haloethyl)sulfonamide is useful as a chemical intermediate in the preparation of herbicides (see, for example, USP Pat. No. 3,205,253), photographic intermediates and other useful compositions. It is known in the art to prepare an N-(2-haloethyl)sulfonamide by the reaction of an alkane or arylene sulfonyl halide with ethylenimine. However, the toxicity of ethylenimine has reduced the applicability of this prior art process. Therefore, it would be useful to find an alternative route to this chemical intermediate. The title compounds are novel precursors of the useful N-(2-haloethyl)sulfonamides or the analogous N-(3-halopropyl)-sulfonamides.

SUMMARY OF THE INVENTION

N-(haloalkyl)sulfonyl imides have been discovered which correspond to the formula

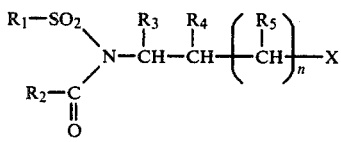

I wherein:
(1) $R_1$ and $R_2$ are independently a $C_1$–$C_{20}$ aryl, alkaryl, aralkyl or alkyl group;
(2) $R_3$, $R_4$ and $R_5$ are independently hydrogen or a methyl group;
(3) n is the integer 0 or 1; and
(4) X is a chloro, bromo or iodo group.

DETAILED DESCRIPTION OF THE INVENTION

The N-(haloalkyl)sulfonyl imides represented by formula I are normally liquids, viscous liquids or low-melting solids. Preferred are the N-(haloethyl)sulfonyl imides, wherein n is the integer 0. $R_1$ is preferably dodecylphenyl, phenyl, methyl or ethyl, with phenyl or methyl being the most preferred. $R_2$ is also preferably phenyl, methyl or ethyl, but ethyl is the most preferred. $R_3$–$R_5$ are each preferably hydrogen moieties. X is preferably a chloro group.

PREPARATION OF SULFONYL IMIDES

These N-(haloalkyl)sulfonyl imides are conveniently prepared by a process comprising reacting a 2-oxazoline or 2-oxazine represented by the formula

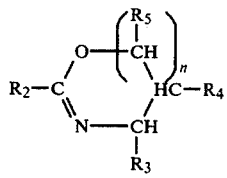

II with a sulfonyl halide represented by the formula $R_1SO_2X$,

III wherein $R_1$–$R_5$, n and X have the aforesaid meaning. Desirably, the oxazoline or oxazine reactant and the sulfonyl halide are reacted in a mole ratio in the range from about 1:1 to about 1:3, preferably in substantially equimolar quantities. A substantial molar excess of an oxazoline reactant produces a polymer instead of the desired product, as is taught in USP Pat. No. 4,120,804.

The reaction is conveniently conducted in a liquid phase and can be conducted in the presence or absence of solvents or diluents. Any organic compound which is substantially inert in the reaction is suitable as a diluent. However, some diluents, such as perchloroethylene, are operable, but for reasons unknown adversely affect the yield of the sulfonyl imide. Representative compounds preferred as diluents include chloroform, methylene chloride, toluene and benzene. The reaction mixture is desirably substantially anhydrous to prevent the formation of undesirable by-products due to hydrolysis.

The manner in which the oxazoline or oxazine reactant is brought together with the sulfonyl halide can affect the yield of the N-(haloalkyl)sulfonyl imide. Desirably, the oxazoline is added to the sulfonyl halide, inasmuch as the reverse order of addition produces initially a substantial molar excess of the oxazoline. The rate of addition of the oxazoline or oxazine is desirably relatively slow, as rapid rates of addition produce substantial amounts of products from side reactions. The optimal rate of addition of the oxazoline or oxazine is not susceptible to quantitative expression, because it is interdependent with other factors, such as reaction temperature and concentration of reactants.

The temperature during the reaction of the oxazoline or oxazine with the sulfonyl halide is desirably in the range from about 20° C. to about 120° C., preferably from about 20° C. to about 100° C. At reaction temperatures above and below the aforementioned desirable range, substantial quantities of the products of side reactions result. Times required for substantially complete reaction depend upon the reaction temperature and the specific reactants, but times from 1 to 8 hours are typical. Prolonged heating of the sulfonyl imide product effects partial deterioration of this product.

Utility of N-(haloalkyl)sulfonyl Imide

The useful chemical intermediate N-(2-haloethyl) sulfonamide can be conveniently prepared from the claimed N-(haloethyl)sulfonyl imide by reaction of this sulfonyl imide with a $C_1$–$C_6$ alkanol, preferably methanol, at reflux. Desirably, the mole ratio of the alkanol or phenol to the sulfonyl imide is in the range from about 1:1 to about 50:1. This process is set out in greater detail in a patent application by Owen, Harmon and Tomalia, filed concurrently herewith, which is hereby incorporated by reference.

An N-(3-halopropyl)sulfonamide can be prepared by the alcoholysis of N-(3-halopropyl)sulfonyl imide in a manner similar to the process described immediately above. This N-(3-halopropyl)sulfonamide would be expected to have utility analogous to N-(2-haloethyl)-sulfonamide.

The following examples are illustrative of the present invention and are not to be construed as limiting the scope thereof in any manner. All parts and percentages are by weight unless otherwise specified.

EXAMPLE 1

A solution of 8.7 grams (0.1 mole) of 2-ethyl-2-oxazoline in 25 milliliters (ml) of methylene chloride is added dropwise over a period of about 20 minutes to a stirred solution of 19.1 grams (0.1 mole) of p-toluene sulfonyl chloride in 75 ml of methylene chloride at 25° C. The resulting exothermic reaction increases the temperature of the reaction mixture to 30° C. during addition. The reaction mixture is then refluxed for 3 hours and stirred for 12 more hours at 20° C. Distillation of the methylene chloride from the mixture at reduced pressure yields 27.8 grams of a honey-colored, viscous liquid.

Analysis of the product by proton magnetic resonance is utilized to identify the product as N-(2-chloroethyl)-N-propionyl-N-p-toluene sulfonyl imide. The yield of this product is 100 percent based on the 2-ethyl-2-oxazoline.

EXAMPLE 2

Anhydrous 2-ethyl-2-oxazoline (24.25 grams, 0.25 mole) is added dropwise to a reaction vessel charged with anhydrous benzene sulfonyl chloride (44.15 grams, 0.25 mole). The contents of the reaction vessel are protected from atmospheric moisture and rapidly stirred. The temperature of the contents of the reaction vessel increases from 21° C. to a temperature of 60° C. during addition of the oxazoline. The reaction mixture is stirred at 20° C. for 3 hours and then at 50° C. to 70° C. for 0.5 hour. 132.3 Grams of a viscous, light yellow liquid product is obtained.

Analysis of the product by proton magnetic resonance identifies it as N-(2-chloroethyl)-N-propionyl-N-benzene sulfonyl imide. The yield of product is 96 percent based on the 2-ethyl-2-oxazoline.

EXAMPLE 3

A solution of 39.6 grams (0.4 mole) of 2-ethyl-2-oxazoline in 75 ml of methylene chloride is added dropwise over a period of 40 minutes to a stirred solution of 45.84 grams (0.4 mole) of methane sulfonyl chloride in 5 ml of methylene chloride. The temperature of the reaction mixture increases from 21° C. to 37° C. during addition of the oxazoline. The reaction mixture is stirred for 2 hours at 36° C. Distillation of the solvent from the mixture at reduced pressure yields 83.7 grams of a pale yellow liquid. This crude product when stored for several weeks at 20° C., crystallizes. Recrystallization from acetone yielded colorless crystals having a melting point of 55° C.–58° C.

Analysis of the product by proton magnetic resonance spectroscopy and elemental analysis identifies it as N-(2-chloroethyl)-N-propionyl-N-methane sulfonyl imide. The yield of the product is 97.9 percent based on 2-ethyl-2-oxazoline.

EXAMPLE 4

Anhydrous 2-phenyl-2-oxazoline (14.7 grams, 0.1 mole) is added dropwise over a period of 20 minutes to a reaction vessel charged with 11.5 grams (0.1 mole) methane sulfonyl chloride, which is rapidly stirred. The temperature of the reaction mixture increases from 25° C. to 28° C. during addition of the oxazoline. The reaction mixture is stirred for 14 hours at 20° C. and then is stirred for an additional hour at 100° C. The product is a viscous liquid, light amber in color, which is determined by proton magnetic resonance to contain N-(2-chloroethyl)-N-benzoyl-N-methane sulfonyl imide in 62 percent yield based on phenyl oxazoline.

What is claimed is:

1. An N-(haloalkyl)sulfonyl imide represented by the formula I

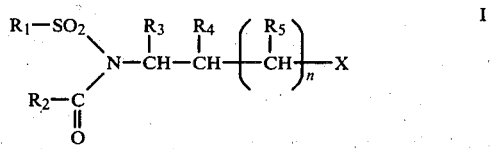

wherein (1) $R_1$ and $R_2$ are independently aryl, alkaryl, aralkyl or alkyl groups having up to 20 carbon atoms
(2) $R_3$, $R_4$ and $R_5$ are independently hydrogen or a methyl group;
(3) n is the integer 0 or 1; and
(4) X in a chloro, bromo or iodo group.

2. The compound defined by claim 1 wherein $R_1$ is methyl, ethyl, dodecylphenyl or phenyl and $R_2$ is methyl, ethyl or phenyl.

3. The compound defined by claim 2 wherein n is the interger 0.

4. The compound defined by claim 3 wherein $R_2$ is ethyl and $R_1$ is phenyl or methyl.

5. The compound defined by claim 4 wherein X is chloro.

6. A process for preparing the N-(haloalkyl)sulfonyl imide as described in claim 1, comprising reacting a 2-oxazoline or 2-oxazine represented by the formula II

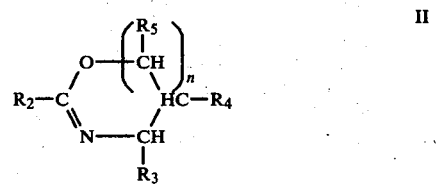

with a sulfonyl halide represented by the formula III $R_1SO_2X$. III

7. The process defined by claim 6 wherein the 2-oxazoline or 2-oxazine and the sulfonyl halide are reacted in a mole ratio from about 1:2 to about 3:2.

8. The process defined by claim 7 wherein the reaction temperature is in the range from about 0° C. to about 120° C.

* * * * *